US012391725B2

(12) United States Patent
Njar et al.

(10) Patent No.: US 12,391,725 B2
(45) Date of Patent: Aug. 19, 2025

(54) METHOD FOR PRODUCTION OF NOVEL GALETERONE ANALOGS AND USES THEREOF

(71) Applicants: Vincent C. O. Njar, Glen Burnie, MD (US); Purushottamachar Puranik, Gaithersburg, MD (US); Francis Murigi, Germantown, MD (US)

(72) Inventors: Vincent C. O. Njar, Glen Burnie, MD (US); Purushottamachar Puranik, Gaithersburg, MD (US); Francis Murigi, Germantown, MD (US)

(73) Assignee: NATIONAL INSTITUTES OF HEALTH (NIH), U.S. DEPT. OF HEALTH AND HUMAN SERVICES (DHHS), U.S. GOVERNMENT, Bethesda, MD (US)

( * ) Notice: Subject to any disclaimer, the term of this patent is extended or adjusted under 35 U.S.C. 154(b) by 0 days.

(21) Appl. No.: 16/310,000

(22) PCT Filed: Jun. 22, 2017

(86) PCT No.: PCT/US2017/038765
§ 371 (c)(1),
(2) Date: Dec. 14, 2018

(87) PCT Pub. No.: WO2017/223320
PCT Pub. Date: Dec. 28, 2017

(65) Prior Publication Data
US 2019/0169227 A1    Jun. 6, 2019

Related U.S. Application Data

(60) Provisional application No. 62/353,103, filed on Jun. 22, 2016.

(51) Int. Cl.
*C07J 75/00*      (2006.01)
*A61K 31/58*      (2006.01)
*C07J 43/00*      (2006.01)
*A61P 35/00*      (2006.01)

(52) U.S. Cl.
CPC ............ *C07J 43/003* (2013.01); *A61K 31/58* (2013.01); *A61P 35/00* (2018.01)

(58) Field of Classification Search
CPC ................................ C07J 43/003; C07J 75/00
See application file for complete search history.

(56) References Cited

U.S. PATENT DOCUMENTS

| | | | |
|---|---|---|---|
| 4,877,892 A | * 10/1989 | Brittelli | C07D 303/36 549/552 |
| 6,177,575 B1 | 1/2001 | Arduengo, III et al. | |
| 2015/0361126 A1 | 12/2015 | Njar et al. | |
| 2016/0038476 A1 | 2/2016 | Njar et al. | |

FOREIGN PATENT DOCUMENTS

| | | |
|---|---|---|
| WO | 2008/068037 A1 | 6/2008 |
| WO | 2014165815 A2 | 10/2014 |
| WO | 2016054472 A1 | 4/2016 |

OTHER PUBLICATIONS

Sun et al., Practical synthesis of 3beta-amino-5-cholestene and related 3beta-halides involving i-steroid and retro-i-steroid rearrangements. Organic Letters, vol. 11(3), pp. 567-570 (Year: 2009).*
Toummini et al., Copper-catalyzed arylation of nitrogen heterocycles from anilines under ligand-free conditions. Chem. Eur. J. vol. 20, pp. 14619-14623 (Year: 2014).*
Partial Supplementary European Search Report, dated Dec. 19, 2019, issued in counterpart European patent application No. 17816212.9 (18 pages; in English).
Puranik Purushottamachar et al., "Identification of Novel Steroidal Androgen Receptor Degrading Agents Inspired by Galeterone 3[beta]-Imidazole Carbamate", ACS Medicinal Chemistry Letters, vol. 7, No. 7, pp. 708-713 (May 23, 2016) (6 pages; in English; cited in European Search Report).
Puranik Purushottamachar et al., "Identification of Novel Steroidal Androgen Receptor Degrading Agents Inspired by Galeterone 3[beta]-Imidazole Carbamte", Supporting Information to ACS Medicinal Chemistry Letters, vol. 7, No. 7, pp. 708-713 (May 23, 2016) (38 pages; in English; cited in European Search Report).
Puranik Purushottamachar et al., "Improved Procedures for Gram-Scale Synthesis of Galeterone 3[beta]- Imidazole and Galeterone 3[beta]-Pyridine Methoxylate, Potent Androgen Receptor/Mnk Degrading Agents", Organic Process Research & Development, vol. 20, No. 9, pp. 1654-1661 (Aug. 10, 2016) (8 pages; in English; cited in European Search Report).

(Continued)

*Primary Examiner* — Brenda L Coleman
(74) *Attorney, Agent, or Firm* — Wenderoth Lind & Ponack, L.L.P.

(57) ABSTRACT

Galeterone and its C-3 analogs are of substantial interest because of their multi-target anticancer activities, including AR and Mnk degrading activities. Provided are novel procedures for gram-scale, high-yield synthesis of C-3 analogs of galeterone, including 3β-(1H-imidazole-1-yl)-17-(1H-benzimidazole-1-yl)-androsta-5,16-diene (galeterone 3β-imidazole) and 3β-(pyridine-4-ylmethoxy)-17-(1H-benzimidazol-1-yl)androsta-5,16-diene (galeterone 3β-pyridine methoxylate).

7 Claims, 3 Drawing Sheets

(56) References Cited

OTHER PUBLICATIONS

International Search Report and Written Opinion dated Sep. 25, 2017 issued in counterpart International application No. PCT/US2017/038765 (8 pages; in English).

Bruno et al., "Synthesis and biological evaluations of putative metabolically stable analogs of VN/124-1 (TOK-001): Head to head anti-tumor efficacy evaluation of VN/124-1 (TOK-001) and abiraterone in LAPC-4 human prostate cancer xenograft model", Steroids, vol. 76, 2011, pp. 1268-1279 (in English, cited in the ISR).

International Preliminary Report on Patentability dated Jan. 3, 2019 issued in counterpart International application No. PCT/US2017/038765 (7 pages; in English).

Extended European Search Report, dated Mar. 17, 2020, issued in counterpart European patent application No. 17816212.9 (16 pages; in English).

* cited by examiner

METHOD FOR PRODUCTION OF NOVEL GALETERONE ANALOGS AND USES THEREOF

CROSS-REFERENCE

This application is a national phase of International Application No. PCT/US2017/038765, filed on Jun. 22, 2017, which claims benefit of U.S. Provisional Application No. 62/353,103, filed on Jun. 22, 2016, the entirety of each of which is herein incorporated by reference.

STATEMENT OF FEDERALLY SPONSORED RESEARCH AND DEVELOPMENT

This invention was made with government support under Grant Number CA195694 awarded by the National Institutes of Health. The government has certain rights in the invention.

TECHNICAL FIELD

The present disclosure relates generally to the field of chemistry, and in particular, to methods for large scale synthesis of galeterone analogs, which are potent androgen receptor degrading agents (ARDAs), and uses thereof.

BACKGROUND

Disruption and/or perturbation of cap-dependent translation is essential for the development of cancers and many fibrotic diseases, the most notable being Alzheimer's disease. Hyper-activation of eukaryotic translation initiation factor 4E (eIF4E), the mRNA 5' cap-binding protein of cap-dependent translation promotes exquisite transcript-specific translation of key mRNAs that are indispensable in cancer initiation, progression and metastases. The oncogenic potential of eIF4E is dependent on serine 209 phosphorylation by MAPK-interacting kinases 1 and 2 (Mnk1/2). Given the implication of Mnk1/2-eIFE axis in the initiation and progressions of all types of solid tumors and hematologic cancers, there is a need for the development of agents for the prevention and treatment of all forms of breast and prostate cancers and other diseases which depend on functional Mnk 1/2.

Androgen receptors (AR) are a well-established target for therapeutic intervention in certain cancers, including prostate cancer, bladder cancer, pancreatic cancer, hepatocellular carcinoma, benign prostatic hyperplasia (BPH) and Kennedy's disease.

Galeterone analogs are of substantial interest because of their multi-target anticancer activities, including AR and Mnk degrading activities. In the course of studies to develop potent androgen receptor degrading agents (ARDAs),[1] the present inventors discovered novel ARDAs that also effectively target oncogenic eukaryotic protein translation, via modulation of Mnk-eIF4E axis, so as to function as Mnk degrading agents (MNKDAs) that suppress oncogenic peIF4E via degradation of Mnk1 and 2. These targets have been implicated in the development, progression, metastasis and drug resistance of a variety of cancers, including prostate[4-8] and pancreatic cancer (pancreatic ductal adenocarcinoma, PDAC).[9-12]

BRIEF SUMMARY

The present disclosure relates generally to the field of chemistry, and in particular, to methods for large scale synthesis of galeterone analogs, and in particular, the present disclosure relates to the large scale synthesis of 3-(1H-imidazole-1-yl)-17-(1H-benzimidazole-1-yl)-androsta-5,16-diene and galeterone 3β-pyridine methoxylate.

In one embodiment, the present disclosure relates to process for preparing 3-(1H-imidazole-1-yl)-17-(1H-benzimidazole-1-yl)-androsta-5,16-diene. The process may comprise a first reaction comprising reacting a compound having Formula 1

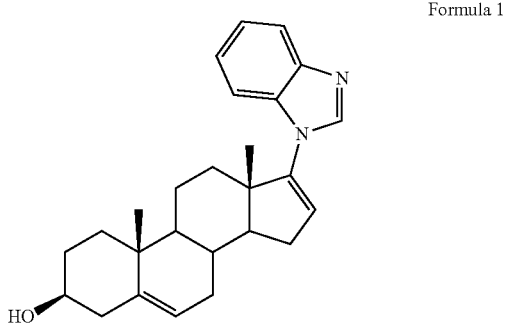 [SMILES: C[C@]12CC[C@H](O)CC1=CCC1C2CC[C@]2(C)C(n3cnc4ccccc43)=CCC12]

Formula 1 to produce 3-azido-17-(1H-benzimidazole-1-yl)androsta-5,16-diene; and a second reaction comprising reacting the 3-azido-17-(1H-benzimidazole-1-yl)-androsta-5,16-diene to produce 3-(1H-imidazole-1-yl)-17-(1H-benzimidazole-1-yl)-androsta-5,16-diene.

In one embodiment, the first reaction may further comprise mesylation of the compound having Formula 1 (1) to produce a mesylate, and azidation of the mesylate (4) to produce the 3-azido-17-(1H-benzimidazole-1-yl)-androsta-5,16-diene.

In one embodiment, the second reaction may further comprise reduction of the 3-azido-17-(1H-benzimidazole-1-yl)-androsta-5,16-diene (7, 8) to produce an amine (9, 10), and cyclization of the amine (9, 10) to produce the 3-(1H-imidazole-1-yl)-17-(1H-benzimidazole-1-yl)-androsta-5,16-diene (2, 5).

In one embodiment, the azidation may comprise contacting the mesylate (4) with an alkali metal azide or an organic azide, so as to perform the azidation in a stereo-selective manner to produce 3α-azido-17-(1H-benzimidazole-1-yl)androsta-5,16-diene (7) or 3β-azido-17-(1H-benzimidazole-1-yl)androsta-5,16-diene. In at least some embodiments, the azidation comprises contacting the mesylate (4) with trimethylsilyl azide in the presence of a suitable Lewis acid and a suitable solvent to produce the 3β-azido-17-(1H-benzimidazole-1-yl)-androsta-5,16-diene. In at least some embodiments, 15 equivalents of the trimethylsilyl azide and 27 equivalents of the suitable Lewis acid are added for 1 equivalent of the mesylate.

In another embodiment, the azidation may comprise contacting the mesylate (4) with sodium azide in the presence of a suitable catalyst and a suitable solvent to produce the 3α-azido-17-(1H-benzimidazole-1-yl)-androsta-5,16-diene (7).

In one embodiment, the reduction and the cyclization may be performed in a stereo-retentive manner.

In another embodiment, the present disclosure relates to a process for preparing galeterone 3β-pyridine methoxylate (3). The process may comprise contacting a compound having Formula 1 (1)

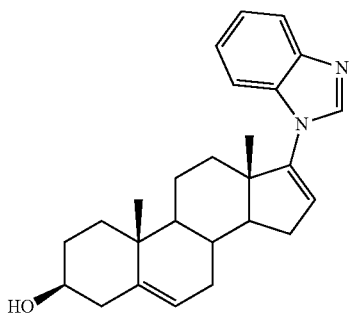

Formula 1

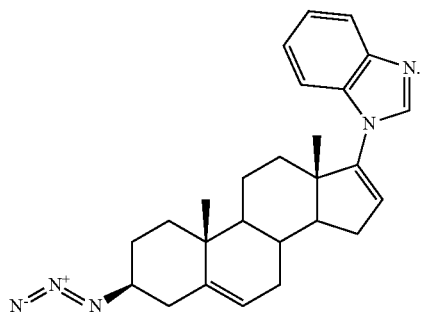

Formula 3

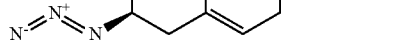

with 4-(bromomethyl)pyridine hydrobromide in the presence of a suitable base, a suitable salt, and at least one suitable solvent to produce the galeterone 3β-pyridine methoxylate.

In at least some embodiments, the solvent may be a mixture of tetrahydrofuran (THF) and dimethylformamide (DMF), and a ratio of THF to DMF (THF:DMF) may be less than 1:2. In at least some embodiments of the present disclosure, the ratio of THF to DMF is 1:16.

In at least some embodiments, the salt is one of lithium carbonate and cesium carbonate. In at least some embodiments, the salt is lithium carbonate.

In at least some embodiments, the base is triethyl amine.

In one embodiment, the process for preparing galeterone 3β-pyridine methoxylate may comprise adding the compound having Formula 1 to a first solvent; treating the compound having Formula 1 in the first solvent with sodium hydride; adding the treated compound having Formula 1 in the first solvent to a second solvent; adding the suitable salt; and then adding the 4-(bromomethyl)pyridine hydrobromide, so as to produce the galeterone 3β-pyridine methoxylate.

In another embodiment, the present disclosure relates to a process for preparing an androgen receptor degrading agent or a MAPK-interacting kinase degrading agent, the process comprising preparing a compound having Formula 2 (7) or a compound having Formula 3 (8):

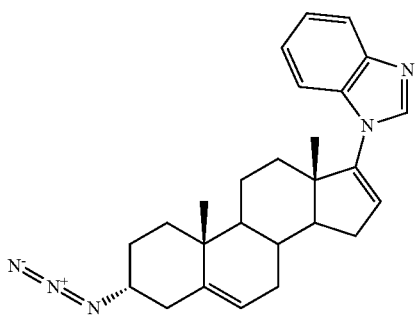

Formula 2

DETAILED DESCRIPTION

Galeterone (1) and its C-3 analogs are of substantial interest because of their multi-target anticancer activities, including androgen receptor (AR) and MAPK-interacting kinase (Mnk) degrading activities. The present disclosure relates to a novel strategy for the synthesis of galeterone analogs, including 3β-(1H-imidazole-1-yl)-17-(1H-benzimidazole-1-yl)-androsta-5,16-diene (galeterone 3β-imidazole) (2) and 3β-(pyridine-4-ylmethoxy)-17-(1H-benzimidazol-1-yl)-androsta-5,16-diene (galeterone 3β-pyridine methoxylate) (3). The present disclosure also relates to a novel strategy for the synthesis of other potential AR degrading agents (ARDAs) and Mnk degrading agents (MNKDAs), including galeterone 3α-imidazole (5) and galeterone 3β-amine (10).

Advantages of the novel synthesis strategies according to the present disclosure include excellent overall yields of the galeterone analogs, simplified production of the compounds, improved production efficiency, and large-scale synthesis of the compounds. The new synthetic procedures of the present disclosure will enable facile production of important galeterone analogs for use in in vitro and in vivo anti-tumor evaluations in models of human prostate, pancreatic, and other human cancers, as well as delinatological diseases. Further, galeterone analogs synthesized according to the present disclosure can be used in the manufacture of a medicament for use in the prevention or treatment of androgen receptor (AR) and/or Mnk-eIF4E associated conditions, including pancreatic cancer, prostate cancer, bladder cancer, hepatocellular carcinoma, benign prostatic hyperplasia (BPH), and Kennedy's disease (spinal and bulbar muscular atrophy), and dermatological diseases such as acne, psoriasis, wrinkling, and photoaged skin.

Figure 1:
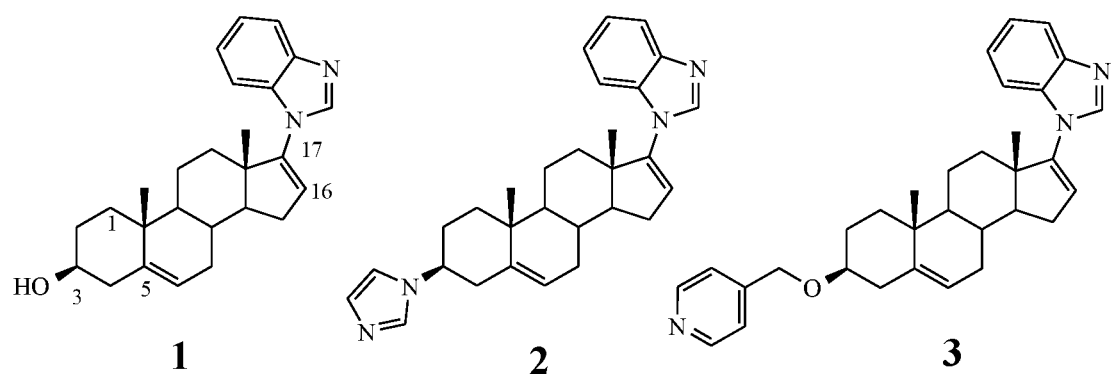
FIG. 1 illustrates a structure of galeterone (1) and its analogs, 3β-(1H-imidazole-1-yl)-17-(1H-benzimidazole-1-yl)-anclrosta-5,16-diene (galeterone 3β-imidazole) (2) and 3β-(pyridine-4-ylmethoxy)-17-(IH-benzitnidazol-1-yl)androsta-5,16-diene (galeterone 3β-pyridine methoxylate) (3).

In the course of studies to design and develop potent androgen receptor degrading agents (ARDAs),[1] using the present inventors' phase 3 clinical candidate, galeterone (1) (FIG. 1)[2,3] as lead, to modulate AR signaling in prostate cancer models,[1] the present inventors discovered that these novel ARDAs also function as Mnk degrading agents (MNKDAs) to suppress oncogenic peIF4E via degradation of Mnk1 and 2. These studies have enabled the present inventors to synthesize and identify 3β-(1H-imidazole-1-yl)-17-(1H-benzimidazole-1-yl)-androsta-5,16-diene (galeterone 3β-imidazole) (2) (FIG. 1) and 3β-(pyridine-4-ylmethoxy)-17-(1H-benzimidazol-1-yl)androsta-5,16-diene (galeterone 3β-pyridine methoxylate) (3) (FIG. 1) as promising new leads with superior anti-prostate cancer activities compared to galeterone (1).[13,14]

However, these two promising lead compounds, galeterone 3β-imidazole (2) and galeterone 3β-pyridine methoxylate (3), were obtained in very low discouraging overall yields of 11 and 12%, respectively. There remains a need to develop an improved and efficient synthesis strategy for the gram scale synthesis of galeterone 3β-imidazole (2) and galeterone 3β-pyridine methoxylate (3).

The present inventors' strategy to improved and efficient procedures for the gram scale synthesis of galeterone 3β-imidazole (2) and galeterone 3β-pyridine methoxylate (3) was based on critical analyses of the present inventors' prior synthetic procedures, including the by-products that were obtained. First, the treatment of imidazole with 3β-mesyl galeterone (4) in refluxing toluene afforded the desired galeterone 3β-imidazole (2) (11%), stereo 3α-isomer (5) (3%), positional 6β-isomer (6) (35%), and uncharacterized elimination products (Scheme 1).[13,14] However, these three products were isolated following tedious flash column chromatography and preparative HPLC procedures. Similar products were also obtained when the reaction was conducted in pyridine at 85° C.

Scheme 1: Influence of nucleophiles on reaction of $\Delta^5$ steroids[a]

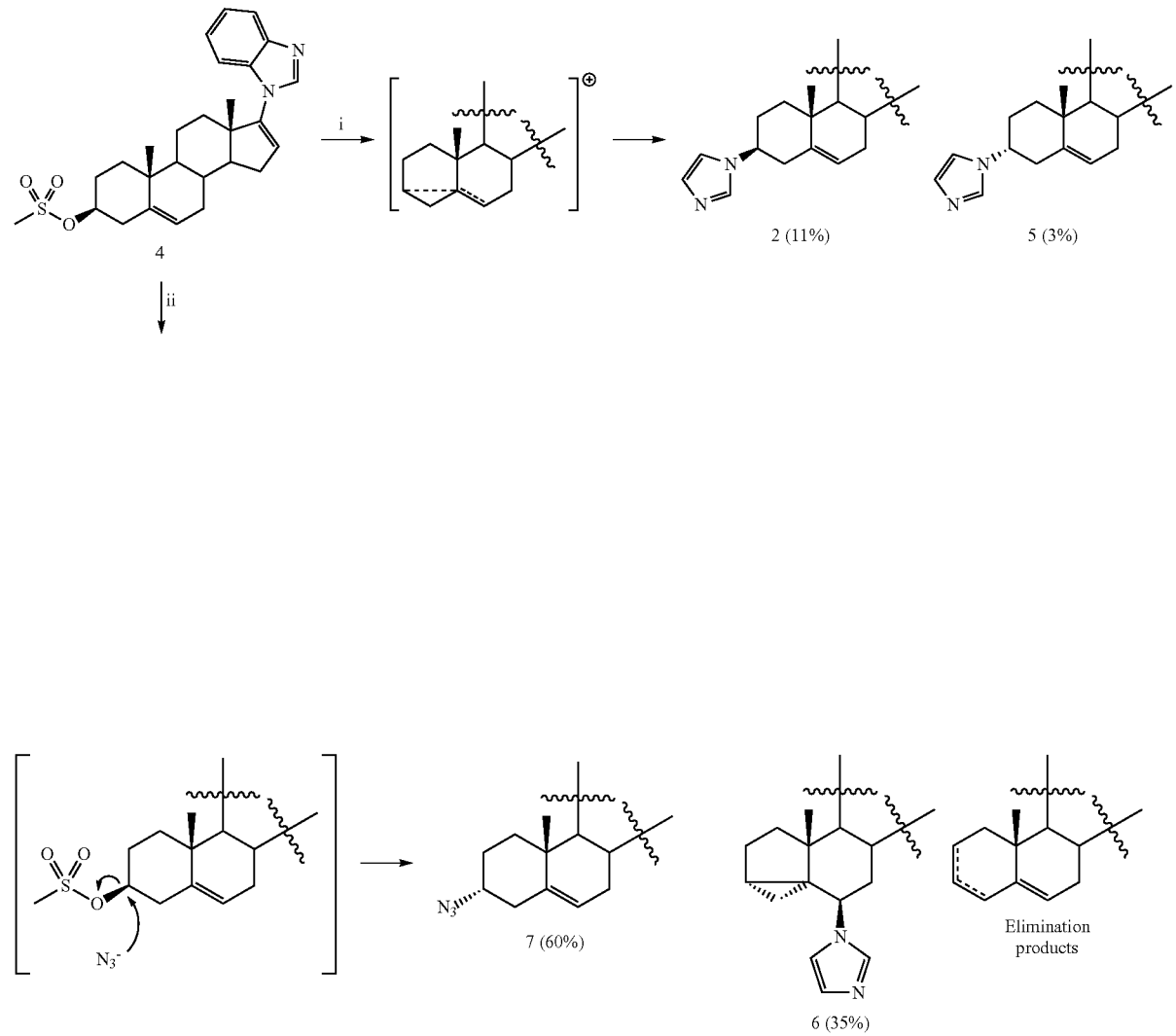

[a]Reagents and conditions: (i) imidazole, PhCH₃, reflux, 12 h or pyridine/DMF, 85° C.; (ii) DMF, NaN₃, 15-crown-5, 80° C., 18 h.

The plausible basis for the formation of stereo/positional isomers in our previous reported synthetic method for compound galeterone 3β-imidazole (2) is depicted in Scheme 1.[13,14] Formation of the 6β-substituted imidazole (6) as major product may be a result of ionization of mesylate prior to the attack of nucleophile at C3 position ($S_N1$ mechanism), which further forms homoallylic hybrid carbonium ion intermediate due to the participation of C5 double bond.[15-19] Attack of nucleophile on hybrid carbonium ion has been demonstrated to be faster at C6 position than at C3 due to the difference in their reactivity.[20] However, strong nucleophile, such as azide, predominantly follows $S_N2$ mechanism to yield stereo inverted C3-azide (7).[21] From these observations, it is clear that the nature of nucleophile has influence on mechanism of $S_N$ reaction of $\Delta^5$ steroids. Weak nucleophile such as imidazole predominantly follow $S_N1$ mechanism while reactive nucleophiles follow $S_N2$ mechanism. Therefore, direct installation of imidazole unit at C3 position in the presence of C5 double bond may be impractical. Thus, synthesis of imidazole ring starting from azide by functional group modification provides an attractive route as will be described in the present disclosure.

Second, for the synthesis of the pyridyl methoxylate (3), the strategy was to improve on the present inventors' reported procedure of Williamson's etherification following treatment of galeterone (1) with 4-(bromomethyl)pyridine hydrobromide in the presence of sodium hydride as base in dimethylformamide (DMF) at 65° C.[13,14] Specifically, the present inventors explored using different solvents and salt effects. This strategy proved successful as will be described in the present disclosure.

The present disclosure provides an efficient four-step synthesis of galeterone 3β-imidazole (2) and a one-step synthesis of galeterone 3β-pyridine methoxylate (3) with remarkably high overall yield (62.8 and 61% overall yields, respectively, in one embodiment of the present disclosure), both from galeterone (1).

The present disclosure also provides a stereospecific synthesis of galeterone 3α-imidazole (5), which can be useful in pharmacokinetics studies of compound galeterone 3β-imidazole (2). In addition, galeterone 3β-amine (10), which is the penultimate precursor of galeterone 3β-imidazole (2), can be obtained at remarkably high overall yield from galeterone (1) (83.9% overall yield in one embodiment of the present disclosure). Galeterone 3β-amine (10) is also proving to be a potent ARDA/MNKDA.

These new and improved procedure for the synthesis of galeterone 3β-imidazole (2) according to the present disclosure does not require column chromatography or multiple crystallizations. Both procedures for target galeterone 3β-imidazole (2) and galeterone 3β-pyridine methoxylate (3) according to the present disclosure are amendable to commercial productions. The efficient production of these new and improved lead ARDAs/MNKDAs will undoubtedly facilitate ongoing anti-tumor efficacy studies.

Synthesis of galeterone 3β-imidazole (2) and galeterone 3α-imidazole (5)

Figure 2:
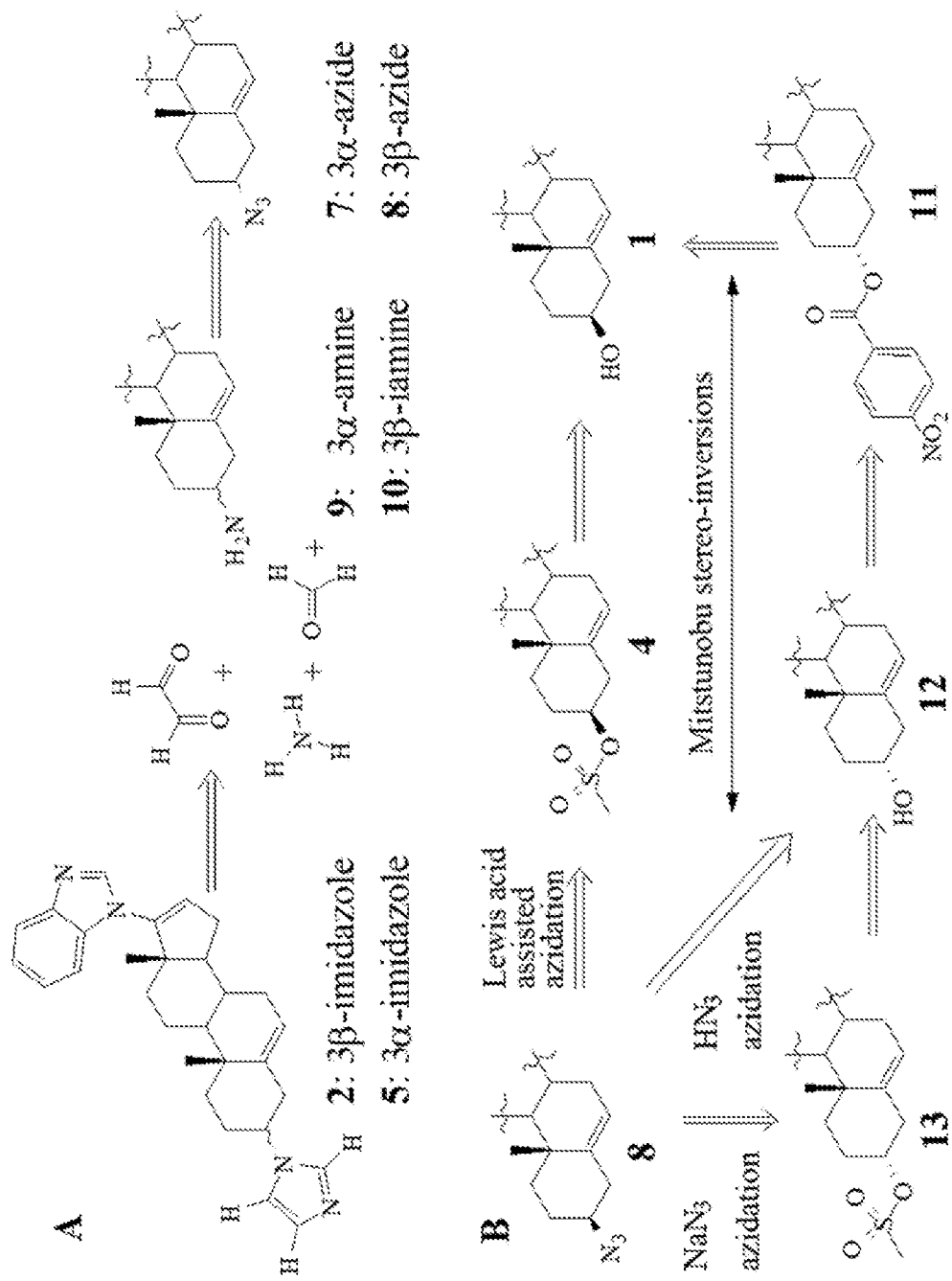
FIG. 2A shows a schematic representation of a retrosynthetic procedure for synthesis of galeterone 3β-imidazole (2) and galeterone 3α-imidazole (5) according to an embodiment of the present disclosure.
FIG. 2B shows a schematic representation of a retrosynthetic procedure for synthesis of key intermediate 3β-azide (8) according to an embodiment of the present disclosure.
Figure 3:
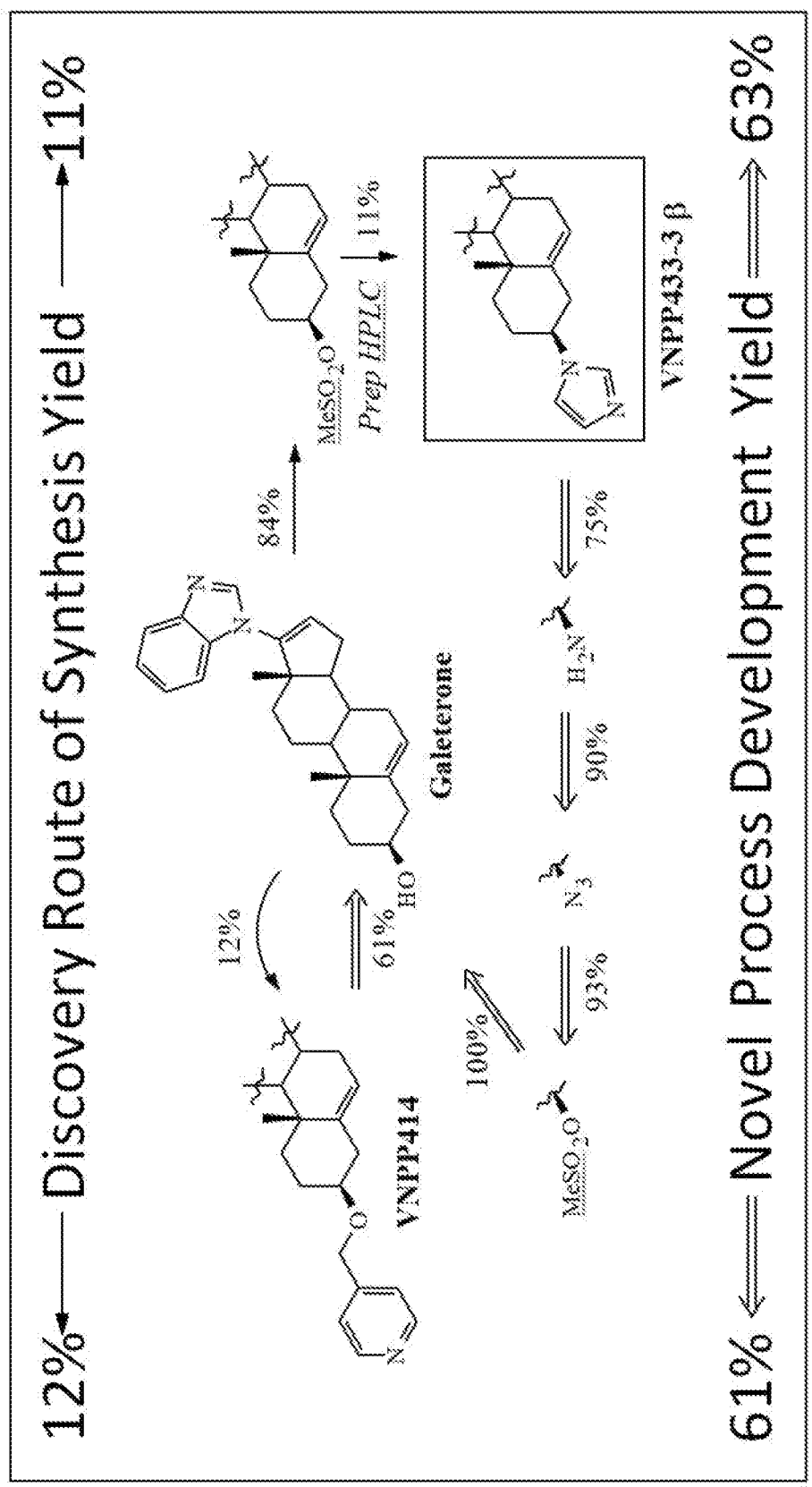
FIG. 3 shows a schematic representation showing the overall yields of galeterone 3β-imidazole (2) and galeterone 3β-pyridine methoxylate (3) according to the present disclosure as compared to known synthesis routes.

The present inventors envisioned and designed a new synthetic route that would enable the tethering of the imidazole moiety to C3 (3α/β-isomers) of galeterone (12/1) as depicted in FIG. 2A. Retro-synthetically, the 3β-imidazole ring can be constructed from 3β-amine (10) by applying Heinrich Debus cyclization method,[22,23] where the 3β-amine (10) would be obtained from selective reduction of key intermediate, 3β-azide (8), without affecting the double bonds in rings B and D.[24]

Next, the present inventors envisioned two possible routes for the synthesis of 3β-azide (8). The first route involves conversion of galeterone (1) to the 3β-mesylate (4) followed by treatment with trimethylsilyl azide (TMSN$_3$) and boron trifluoride etherate (BF$_3$.OEt$_2$) in dichloromethane (DCM). This procedure is termed Lewis acid mediated i-steroid/retro-i-steroid rearrangement method (FIG. 2B).[24] Alternatively, 3β-azide (8) can be obtained from epi-galeterone (12) either by Mitsunobu method of using hydrogen azide or via treatment of α-mesyl derivative (13) with NaN$_3$ (FIG. 2B). Both routes involving epi-galeterone (12) are known to produce the azide as major product, with inversion of configuration.[21,25]

The Heinrich Debus method for the synthesis of imidazole ring from primary amines is widely reported in the literature.[22,26,27] However, the applicability of the Heinrich Debus method to aminosteroids is novel.

(a) Synthesis of Galeterone 3α-imidazole (5)

Before initiating any efforts toward the stereospecific synthesis of the key intermediate, 3β-azide (8), the present inventors considered it prudent to first evaluate the synthetic feasibility of imidazole ring from amine at C3 position of steroid using easily accessible 3α-azide (7), previously reported by the present inventors' group.[21] In addition, the resultant galeterone 3α-imidazole (5), a possible metabolite of galeterone 3β-imidazole (2) would be valuable during pharmacokinetics (PK) and other in vivo studies.

As illustrated in Scheme 2, the procedure begins with the mesylation of galeterone with a suitable mesylating agent, for example, a mesyl halide (for example, mesyl chloride) and the like. Although the present inventors have reported the milligram scale synthesis of 3β-mesyl galeterone (4), at 84% yield, using pyridine as solvent and base, its application in gram scale yielded intractable mixture of products.[1] The present inventors have found that remarkably, by replacing DCM as solvent and using triethyl amine (TEA) as base,[24] they are able to obtain 3β-mesyl galeterone (4) at 99.6% yield after simple solvent removal, water wash of residue solids, filtration and drying under vacuum.

The azidation of 3β-mesyl galeterone (4) to 3α-azide (7) is achieved in relatively shorter time (18 hours) in comparison to the present inventors' previous method (48 hours, 60% yield),[21] by conducting the reaction in the presence of catalytic amount of a suitable catalyst, for example, 15-Crown-5 (yield 59.8%).[28] The azidation is performed by contacting the 3β-mesyl galeterone (4) with a suitable azidating agent, for example, an alkali metal azide (for example, NaN$_3$) and the like, in the presence of a suitable solvent (for example, DMF and the like). The azidation is performed at a suitable temperature, for example about 80° C.

For the reduction of 3α-azide (7) to 3α-amine (9), LiAlH$_4$ in ether method has been reported to give a good yield (60%).[24] Considering the requirement of anhydrous condition and difficulties in handling pyrophoric reagent in scale-up, there is a need for a nonhazardous reduction method. Application of the Staudinger method of azide reduction, using PPh$_3$ in tetrahydrofuran (THF)/methanol (MeOH)/water (4:4:1) at 60° C. smoothly converts 3α-azide (7) into 3α-amine (9) within 10 hours.[29] The product, in 66.7% yield, is isolated by simple acid-base workup.

The cyclization of 3α-amine (9) into 3α-imidazole (5) is achieved by reacting with aqueous ammonia, formaldehyde and alyoxal at a suitable temperature (for example, 70° C.) for a suitable length of reaction time (for example, 5 hours).[26] As in the case of amine, the imidazole product is also isolated by acid base workup and further purified by passing through a plug of silica using 1-5% metanol in ethyl acetate. The pure product obtained is reprocessed with acid-base to obtain solvent free product in 70.7% yield.

This route of synthesis gave 28.1% overall yield of galeterone 3α-imidazole (5) starting from 3β-mesyl galeterone (4) in three steps (β-mesyl →α-$N_3$→α-$NH_2$→α-imidazole). By these test reactions using 3α-azide (7), the present inventors have not only established the viability of the synthetic strategies of the present disclosure, but also established the reaction conditions and purification procedures which are extended to the synthesis of the desired galeterone 3β-imidazole (2).

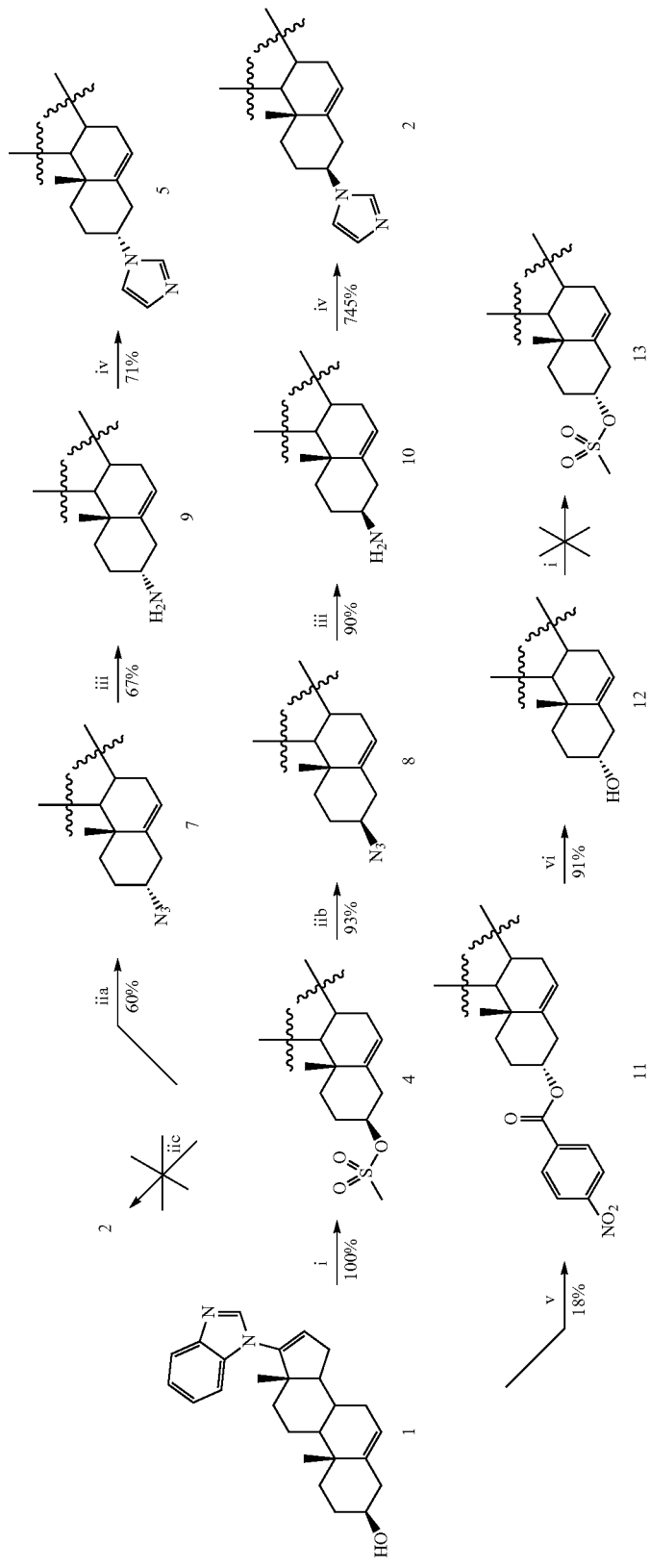

(b) Synthesis of Galeterone 3β-imidazole (2)

Having demonstrated the working synthetic strategy, the present inventors turn to the synthesis of key intermediate 3β-azide (8).

As illustrated in Scheme 2, the synthesis begins with the mesylation of galeterone with a suitable mesylating agent, for example, a mesyl halide (for example, mesyl chloride) and the like. The mesylation may occur in the presence of a suitable solvent (for example, DCM) and a suitable base (for example, triethyl amine (TEA)), as described above. 3β-mesyl galeterone (4) can be obtained at a remarkably high yield (for example, 99.6% yield as described above) after simple solvent removal, water wash of residue solids, filtration and drying under vacuum.

3β-mesylate (4) then undergoes azidation to produce 3β-azide (8). Recently, Sun et al. reported a practical synthesis for the conversion of cholest-5-en-3β-ol methanesulfonate to 3β-amino-5-cholestene with retention of configuration in 93% yield).[24] The method involves the use of trimethylsilyl azide (TMSN$_3$) in the presence of a Lewis acid which led to C3 steroidal azidation with complete stereo-retention.

The present inventors attempted this method on 3β-mesylate (4) using the reported ratio of reagents and also doubled the quantity of reagents with longer duration of reaction time. Neither of these reaction conditions indicated formation of the expected 3β-azide product (8). The present inventors therefore pursued the epi-galeterone (12) route for the synthesis of 3β-azide (8), as illustrated in Scheme 2. The desired epi-galeterone (12) was obtained from galeterone (1) by Mitsunobu stereo-inversion method.[30] This involves the formation of nitrobenzoicacid 3α-epiester (11) and its hydrolysis with aqueous NaOH to obtain epi-galeterone (12). This stereo-inversion method required cumbersome purification procedure due to the polar nature of substrate, product, and by-products, such as, PPh$_3$O, diethyl 1,2-hydrazinedicarboxylate of reagents PPh$_3$, DEAD. As a result, it provided only 16.5% yield of epi-galeterone (12) from galeterone (1).

For the conversion of epi-galeterone (12) to the desired 3β-azide (8), the present inventors only attempted mesylation route (FIG. 2B, Scheme 2) to avoid hazardous nature of hydrogen azide in the Mitsunobu method. Unfortunately, the attempts to synthesize 3α-mesyl (13) resulted in elimination products along with intractable adducts.

This unexpected difficulty in functional group modifications inspired the present inventors to revisit the i-steroid and retro-i-steroid rearrangement method for steroidal 3β-azide synthesis. As stated above, Sun et al. reported that the method worked efficiently on 3β-cholesteryl mesylate while using 1 equivalent of TMSN$_3$ and 2 equivalents BF$_3$.OEt$_3$ in DCM.[24] Sun et al. also stated that no reaction was observed when solvents bearing heteroatoms that function as Lewis base were used.[24] Based on these data, the present inventors reasoned that the failure of earlier efforts to synthesize 3β-azide (8) from 3β-mesylate (4) could be due to presence of heteroatoms in the substrate 3β-mesylate (4) (i.e., benzimidazole hetero-nitrogen atoms).

Thus, the present inventors hypothesized that the amount of BF3.OEt$_2$ used in the earlier reactions could be consumed by nitrogen atoms of benzimidazole ring of compound 3β-mesylate (4). To evaluate this possibility, the present inventors set up a reaction using 10 equivalents of BF3.OEt$_2$ which indicated very little progress in the reaction as evidenced by thin layer chromatography (TLC) and was incomplete even after longer duration of reaction time (48 hours).

To determine the optimum conditions required for this azidation reaction, the present inventors evaluated various ratio of TMSN$_3$/BF$_3$.OEt$_3$. The present inventors eventually found that the best yield (93.1%) was obtained when 15 and 27 equivalents of TMSN$_3$ and BF$_3$.OEt), respectively, were used for 1 equivalent of 4 in anhydrous DCM at about 22° C. for 5 hours.

More particularly, as illustrated in Scheme 2, the azidation of 3β-mesylate (4) to 3β-azide (8) is performed by contacting the 3β-mesylate (4) with a suitable azidating anent, for example, an organic azide (for example, TMSN$_3$) and the like, in the presence of a suitable solvent (for example, DCM and the like), a suitable Lewis acid (for example, BF$_3$ as the adduct BF$_3$.OEt$_2$). The azidation is performed at a suitable temperature for a suitable length of reaction time. Pure Lewis acid salt free 3β-azide product (8) was isolated by filtration after neutralizing the reaction mixture (exothermic) as well as breaking the complex of product with Lewis acid with aqueous NaOH for a suitable length of time. In one non-limiting embodiment of the present disclosure, TMSN$_3$ is added 3β-mesylate (4) in DCM, followed by addition of BF$_3$.OEt$_2$. The reaction is allowed to progress at about 22° C. for about 5 hours. The reaction mixture is then neutralized in an aqueous NaOH at about 22° C. for 6 hours.

Finally, reduction of 3β-azide (8) to 3β-amine (10) (90.5%) followed by cyclization, as described above for 3α-amine (7) gave the desired 3β-imidazole (2) in 74.8% yield. Surprisingly, both Staudinger azide reduction and Heinrich Debus method of imidazole synthesis gave better yield in shorter time in the case of β-epimer in comparison to α-epimer. This may be due to easy accessibility of equatorial functions in comparison to axial on steroid scaffold.[31]

Functional group modification β-mesyl →β-N$_3$→β-NH$_2$→β-imidazole) proceeded rapidly and in high yield (overall yield 62.8%) with complete retention of configuration. The whole process was repeated twice to confirm the yields with standard deviation of 2%.

Synthesis of galeterone 3β-pyridine methoxylate (3)

To improve on the present inventors' previously reported low yield synthesis of galeterone 3β-pyridine methoxylate (3),[13,14] the present inventors initially attempted the synthesis following the procedure reported by Jilka et al.[32] where galeterone (1) in THF was treated with sodium hydride (NaH) at 0° C. and stirred at room temperature for 10 minutes followed by addition of 4-(bromomethyl)pyridine hydrobromide solution [14; THF/DMF (1:1), TEA]. The product was isolated in low yields of 24%, although it was slightly higher than the present inventors' previously 12% yield reported in recent reports.[13,14] There remains a need to improve the synthesis of galeterone 3β-pyridine methoxylate (3). In an effort to improve the product yield, the present inventors investigated DMF and DMSO as alternative reaction solvents to THF/DMF mixture, but insignificant product formation improvement was observed by TLC analysis.

Salts are known to affect the transition state of $S_N2$ reactions positively.[33] In attempting to investigate salt effect in the substrate reaction, the present inventors incorporated lithium carbonate (Li$_2$CO$_3$) which concurrently eliminated neutralization of 4-(bromomethyl)pyridine hydrobromide solution (14) with TEA.

The procedure developed according to the present disclosure is depicted in Scheme 3:

Scheme 3: Synthesis of galeterone 3β-pyridine methoxylate (3)[a]

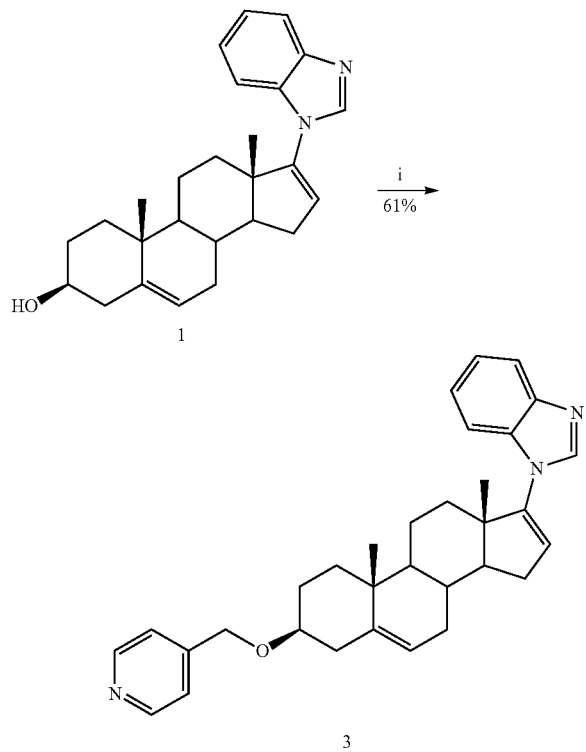

[a]Reagents and conditions: (i) NaH, Li$_2$CO$_3$, DMF/THF, 0° C., 4-(bromomethyl) pyridine hydrobromide (14), rt, 18 h.

Galeterone (1) in THF was treated with NaH at a suitable temperature (for example, 0° C. in one embodiment of the present disclosure). After the reaction is allowed to proceed for a suitable length of time, DMF is added at a suitable temperature. A suitable salt (for example, lithium carbonate (Li$_2$CO$_3$), cesium carbonate (Cs$_2$CO$_3$), and the like) is then added to the reaction mixture at a suitable temperature, followed by reagent 4-(bromomethyl)pyridine hydrobromide solution 14 to give the product in good yields (61-64%) and unreacted galeterone (1) is recovered. The color of the reaction mixture after addition of all reactants should remain colorless for about one hour and gradually change to dark red after 18 hours.

In one non-limiting embodiment of the present disclosure, NaH is added to galeterone (1) in THF at 0° C., followed by addition of DMF at 0° C. after one minute. The reaction mixture is placed at 0° C. and Li$_2$CO$_3$ is added, followed by addition of reagent 4-(bromomethyl)pyridine hydrobromide solution 14.

The reaction done with DMF as the solvent produced a green/blue reaction mixture color and no product formed irrespective of the reaction duration, while THF revealed low product formation as analyzed by TLC.

The ratio of DMF to THF may be in the range of from 1:2 to 1:16. Preferably, the DMF to THF ratio is 1:16, which is applicable to both milligram (≥250 mg) and gram (1-5 g) scales reactions. If the ratio of DMF to THF is greater than 1:2, there may be a risk of low product yield.

When the solvent is DMSO and the ratio of DMSO and THF in the solvent mixture is 1:2, no product formed.

Cesium carbonate salt gave 50% of product.

The present inventors found that reaction conditions, for example, the order of the reagent and solvent addition, as well as temperature control during addition, is crucial to obtaining the desired yield of the desired product and the percent completion of the reaction.

EXAMPLES

General: Galeterone used in this process development was provided by Takai Pharmaceutical Inc. (TPI). All other reagents were obtained from Sigma-Aldrich and were used without further purification. Room temperature means ~22° C. Reactions were conducted using oven dried glassware under a positive pressure of argon. Anhydrous tetrahydrofuran (THF, 99.8%, SIGMA™), triethylamine (TEA, 99.5%, SIGMA™), anhydrous N,N-dimethylformamide (DMF, 99.8%, ACROS™), anhydrous Dimethyl sulfoxide (DMSO, 99.8%, SIGMA™) were used as supplied. Reactions were monitored by analytical thin-layer chromatography on Silica plate TLC aluminum baked plates coated with 200 μm silica gel, indicator F254 and Flash Column Chromatography (FCC) was performed using silica gel (230-400 mesh, 60 Å). Melting points were recorded on Fisher-Johns melting point apparatus and are uncorrected. NMR spectra were recorded on a Bruker Ascend 400 spectrometer, and chemical shifts δ are expressed in ppm relative to TMS as internal reference ($^1$H and $^{13}$C). $^1$H and C NMR data were analyzed and reports were generated by using ACD/NMR Processor Academic Edition. High-resolution mass spectrometry was obtained on Bruker 12T APEX-Qe FTICR-MS instrument by positive ion ESI mode by Isaiah Ruhl, Interim Facility Director, College of Sciences Major instrumentation cluster, Old Dominion University, Norfolk, VA. Purity of intermediates and final compound were determined by HPLC method.

Purity check of compounds used for biological activity (HPLC Chromatography): The purity of compounds determined by reverse phase on LC system of Waters Acquity Preparative HPLC 2535 Quaternary Gradient Module coupled with a Waters 2489 UV/visible photodiode array detector operated at 254 nm using Novapak C18 4 μl, 3.9×150 mm column as the stationary phase at room temperature. Mobile phase-A comprised of Water/MeOH/ CH$_3$CN (20:50:30 v/v/v+1 mL of TEA) and maintained isocratically at the flow rate of 2.5 mL/min for mesyl (4), imidazoles derivatives (compounds 2 and 5), and epigaleterone (12) compound. Where purity of azide (7, 8) and amines (9, 10) were determined by applying gradient method of using above Mobile Phase-A and Mobile Phase-B contained methanol with flow rate of 1.5 mL/min (see chromatograms for detail in SI). Similarly, a gradient method applied for aaleterone 3β-pyridine methoxylate (3) by using Mobile Phase-C comprised of 10 niM ammonium acetate (NH$_4$OAc) buffer solution and Mobile Phase-D comprised of Water/MeOH/CH$_3$CN (35:35:30 v/v/v+20 μL of TEA+77 mg of NH$_4$OAc) with flow rate of 0.8 mL/min Purity of all compounds are >96.5%.

3β-(1H-imidazol-1-yl)-17-(1H-benzimitlazol-1-yl)-androsta-5,16-diene (2): A mixture of amine (10) (6.5 g, 16.78 mmol), ammonia (25% aq., 3.9 mL, 28 mmol), distilled water (5 mL) and MeOH (120 mL) at ~22° C. was added glyoxal trimer dihydrate (5.5 g, 26 mmol) and formaldehyde (37% aq., 2.14 mL, 26 mmol) simultaneously. The reaction mixture was immediately taken to 70° C. (pre heated oil bath) and stirred for 2 hours, and then additional half more quantity of ammonia and formaldehyde added and continued. When amine (10) was consumed as evidenced by TLC (~3 hours), reaction mixture evaporated under vacuum at 60° C., reconstituted with 120 mL of DCM and extracted with 1N HCl (60 mL×2). Aqueous phase collected washed with DCM and neutralized with 1N aq. NaOH and resulting precipitate is extracted with ethyl acetate (60 mL×2). Biphasic solution passed through a plug of celite, organic phase collected, washed with water and evaporated to obtain yellowish red sticky crude product. Sticky mass absorbed on silica (1.5 w/w) and passed through a short bed of silica using 1-5% methanol in ethyl acetate to obtain a cream solid compound 2. Product is reprocessed with acid-base and collected by filtration to obtain solvent free compound 2 (5.5 g, 74.8%), mp 180-184° C.; $R_f$=0.21 (DCM/MeOH/TEA, 10/0.5/0.025); $^1$H NMR (400 MHz, CDCl$_3$) δ 1.04 (s, 3 H, 18-CH$_3$) 1.14 (s, 3 H, 19-CH$_3$) 3.87-4.00 (in, 1 H, 3α-H) 5.50 (d, J=5.14 Hz, 1 H, 6-H) 5.96-6.03 (in, 1 H, 16-H) 7.01 (s, 1 H, Ar'-4-H) 7.10 (s, 1 H, Ar'-5-H) 7.27-7.35 (m, 2 H, 6-Hs) 7.46-7.54 (m, 1 H, Ar-7-H) 7.67 (br. s., I H, Ar'-2-H) 7.79-7.86 (m, 1 H, Ar-4-H) 7.97 (s, 1 H, Ar-2-H); 13C NMR (101 MHz, CDCl$_3$) δ 147.1, 143.2, 141.6, 140.0, 135.2, 134.5, 129.0, 124.0, 123.4, 122.5, 122.2, 120.2, 116.8, 111.1, 57.4, 55.8, 50.5, 47.2, 40.5, 37.8, 36.9, 34.8, 31.0, 30.2, 30.2, 29.9, 20.6, 19.3, 16.0; HPLC: $t_R$ 2.26 min 97.58%; HRMS calcd 339.2856 ($C_{26}H_{34}N_4H^+$), found 339.3856.

3β-(pyridine-4-ylmethoxy)-17-(1H-benzimidazol-1-yl)-androsta-5,16-diene (3): Sodium hydride {3.0 g, 125 mmol, 10 eq. (5.0 g of 60% NaH in oil)} was added to a solution of galeterone (1, 5.0 g, 12.9 mmoL, 1 eq.) in THF (80 mL) at 0° C. under argon atmosphere. A white precipitate formed and after stirring for one minute, DMF (5.0 mL) was added and the reaction mixture was allowed to stir for 10 minutes at room temperature. The reaction mixture was placed at 0° C. and lithium carbonate (5.0 g, 67.7 nunoL, 5 eq.) was added, followed immediately by 4-(bromomethyl)pyridine hydrobromide (14, 10 g, 39.5 mmoL, 3 eq.) and the reaction mixture was allowed to stir at 0° C. for 30 minutes. The reaction mixture was removed from 0° C. and stirring continued at ambient temperature for 18 hours under argon atmosphere. The color of the reaction mixture changed from clear to dark red during the 18-hour period. After 18 hours, the reaction mixture was placed at 0° C., water (30 mL) was added to quench unreacted NaH, and the mixture was stirred for 10 minute. Volatile (THF) were removed in vacuo and water (70 mL) was added to the residue aqueous phase. The aqueous phase was extracted with ethyl acetate (EtOAc) (150 mL×3). Ethyl acetate extract was washed with brine (80 mL×2), dried with anhydrous Na$_2$SO$_4$ and concentrated in vacuo to give a dark red crude product. Purification by flash chromatography using 3% MeOH/EtOAc as eluent afforded compound galeterone 3β-pyridine methoxylate (3) as a white solid (3.78 g, 7.88 mmoL, 61%), mp 177-179° C. $R_f$=0.31 (5% MeOH/EtOAc). $^1$H NMR (400 MHz, CDCl$_3$) δ 1.02 (s, 3H, 18-CH$_3$), 1.09 (s, 3H, 19-CH$_3$), 1.11 (m, 2H), 1.56 (m, 2H), 1.77 (rn, 7H), 1.99 (d, J=12.6 Hz, 1H), 2.17 (m, 2H), 2.33 (t, J=11.3 Hz, 1H), 2.44 (t, J=16.4 Hz, 2H), 3.30 (m, 1H, 3α-H), 4.59 (s, 2H, 2"-CH$_2$), 5.42 (d, J=5.0 Hz, 1H, 6-H), 5.98 (m, 1H, 16-H), 7.29 (m, 4H, aromatic and pyridinyl-Hs), 7.49 (m, 1H, aromatic-H), 7.81 (m, 1H, aromatic-H), 7.96 (s, 1H, T-H), 8.57 (d, J=5.4 Hz, 2H, pyridinyl-Hs). $^{13}$C NMR (100 MHz, CDCl$_3$) δ 19.3, 20.6, 28.3, 30.2, 30.3, 31.1, 34.8, 37.0, 37.1, 39.0, 47.2, 50.5, 55.8, 68.3, 79.1, 111.1, 120.2, 121.2, 121.7, 122.4, 123.3, 124.0, 134.5, 141.0, 141.6, 143.2, 147.1, 148.2, 149.8. HPLC: $t_R$ 3.721 min 100%; HRMS calcd 502.2828 ($C_{32}H_{37}N_3O_2Na^+$, found 502.2834.

3β-Mesyloxy-17-(1H-benzimidazole-1-yl)-androsta-5,16-diene (4): To a solution of galeterone (12 g, 30.9 mmol) in anhydrous DCM (100 ml) at 4° C. was added TEA (6.46 mL, 46.36 mmol), followed by the addition of a solution of mesyl chloride (2.87 mL, 37.08 mmol) in anhydrous DCM (30 mL) drop wise. The reaction was continued at 4° C. for 30 minutes and then stirred at ~22° C. for total of 16 hours. The reaction mixture was concentrated in vacuo, residue solid treated with water, filtered and dried to afford 4 (14.35 g, 99.6%) as a white solid, mp 172-174° C.; $R_f$=0.4 (DCM/EtOH/TEA, 10:0.25:0.025); $^1$H NMR (400 MHz, CDCl$_3$) δ 1.02 (s, 3 H, 18-CH$_3$), 1.08 (s, 3 H, 19-CH$_3$), 3.02 (s, 3 H, Mesyl-CH$_3$), 4.49-4.61 (m, 1 H, 3α-H), 5.49 (d, J=4.89 Hz, 1 H, 6-H), 5.99 (m, 1H,16-H), 7.28-7.34 (m, 2 H, Ar-5, 6-Hs), 7.47-7.52 (m, 1 H, Ar-7-H), 7.79-7.85 (m, 1 H, Ar-4-H), 7.95 (s, 1 H, Ar-2-H); 147.1, 143.2, 141.6, 139.1, 134.5, 124.0, 123.4, 123.1, 122.4, 120.2, 111.1, 81.6, 55.7, 50.2, 47.2, 39.1, 38.8, 36.7, 36.6, 34.7, 31.0, 30.2, 28.8, 20.6, 19.1, 16.0; HPLC: $t_R$ 1.62 min 97.69%; HRMS calcd 955.4472 ($C_{21}H_{34}N_2O_4S)_2Na^+$ (note: dimer formation), found 955.4468.

3α-(1H-imidazol-1-yl)-17-(1H-benzimidazol-1-yl)androsta-5,16-diene (5): A mixture of amine 9 (0.2 g, 0.516 mmol), ammonia (25% aq., 0.12 mL, 0.856 mmol), distilled water (0.15 mL) and MeOH (7.5 mL) at ~22° C. was added glyoxal trimer dihydrate (0.17 g, 0.8 mmol) and formaldehyde (37% aq., 0.067 mL, 0.82 mmol) simultaneously. The reaction mixture immediately taken to 70° C. (pre heated oil bath) and stirred for 3 hours before the addition of one more portion of glyoxal trimer dihydrate (0.16 g), formaldehyde (0.067 mL) and ammonia (0.12 mL), and continued stirring at 70° C. for 2 hours. When 3α-amine (9) was consumed as evidenced by TLC, reaction mixture allowed to cool, filtered through celite, residue washed with MeOH (5 mL), and combined methanolic solutions evaporated. Resulting sticky crude product was reconstituted with DCM (20 mL) and washed with water, then extracted with IN HCl solution (10 mL×2). Combined acid extracts were washed with DCM (7.5 mL×2), and then aqueous layer basified to neutralization with saturated NaHCO$_3$ solution to obtain yellow solid. Colored product was dissolved in DCM, absorbed on silica (1.5 eq. w/w) and passed through a short bed of silica using 1-5% methanol in ethyl acetate to obtain a cream solid, which reprocessed with acidbasification to obtain solvent free 5 (0.16 g, 70.7%), mp 207-209° C.; $R_f$=0.2 (DCM/MeOH/TEA, 10/0.5/0.025); $^1$H NMR (400 MHz, CDCl$_3$) δ 1.02 (s, 3 H, 18-CH$_3$), 1.14 (s, 3 H, 19-CH$_3$), 4.41 (br. s., 1 H, 3β-H), 5.56 (d, J=3.18 Hz, I H, 6-H), 5.94-6.06 (m, 1 H, 16-H), 7.03 (d, J=3.67 Hz, 2 H, Ar'-4, 5-Hs), 7.28-7.37 (m, 2 H, Ar-5, 6-Hs), 7.45-7.54 (m, 1 H, Ar-7-H), 7.73 (s, 1 H, Ar'-2-H), 7.77-7.86 (m, 1 H, Ar-4-H), 7.95 (s, 1 H, Ar-2-H); $^{13}$C NMR (101 MHz, CDCl$_3$) δ 147.0, 143.2, 141.6, 139.1, 136.7, 134.5, 128.5, 124.1, 123.4, 123.3, 122.4, 120.2, 118.6, 111.1, 55.7, 52.9, 50.1, 47.2, 37.2, 35.9, 34.7, 32.2, 31.1, 30.2, 30.1, 28.3, 20.2, 19.3, 16.0; HPLC: $t_R$ 1.83 min 98.83%; HRMS calcd 439.2856 ($C_{26}H_{34}N_4H^+$), found 439.3856.

3α-Azido-17-(1H-benzimidazole-1-yl)-androsta-5,16-diene (7): NaN$_3$ (0.42 g, 6.43 mmol) was added to a stirred solution of mesylate 4 (1 g, 2.14 mmol) and 15-crown-5 (0.005 g, 0.21 mmol) in anhydrous DMF (7.5 mL). The mixture was heated at 80° C. for 18 hours. After cooling, the reaction mixture was poured into ice water mixture, stirred for 30 minutes, filtered and dried to obtain 0.86 g of crude product. Pure product was obtained after crystallization from ethyl acetate and petroleum ether (0.53 g, 69.8%), mp 164-165° C.; $R_f$=0.21 (petroleum ether: ethyl acetate, 2:1);

¹H NMR (400 MHz, CDCl₃) δ 1.01 (s,3 H, 18-CH₃), 1.06 (s, 3 H, 19-CH₃), 3.91 (t, J=2.81Hz, 1 H, 3β-H), 5.46 (d, J=5.14 Hz, 1 H, 6-H), 5.93-6.01 (m, 1 H,16-H), 7.27-7.34 (m, 2 H, Ar-5, 6-Hs), 7.46-7.52 (m, 1 H, Ar-7-H), 7.78-7.84 (m, 1 H, Ar-4-H), 7.97 (s, 1 H, Ar-2-H); ¹³C NMR (101 MHz, CDCl₃) δ 147.1, 143.2, 141.6, 138.5, 134.5, 124.1, 123.3, 122.5, 122.4, 120.2, 111.1, 58.1, 55.7, 50.2, 47.2, 37.3, 36.0, 34.8, 33.5, 31.0, 30.2, 30.2, 26.0, 20.3, 18.9, 16.0; HPLC: $t_R$ 7.02 min 98.16%; HRMS calcd 414.2652 ($C_{26}H_{31}N_5H^+$), found 414.2652.

3β-Azido-17-(1H-benzimidazole-hypandrosta-5,16-diene (8): To a solution of mesylate 4 (13 g, 27.8 mmol) in anhydrous DCM (100 mL) was added TMSN₃ (55.5 mL, 418.2 mmol), followed by BF₃.OEt₂ (71.23 mL, 752.8 mmol). The reaction was stirred at ~22° C. for 5 hours. When starting material was completely consumed as evidenced by TLC (petroleum ether:ethyl acetate, 2:1; $R_f$=0.44 for product and Lewis acid complex), reaction was slowly poured into RB flask on ice bath containing aqueous 2M NaOH (750 ml) and stirred at ~22° C. for 6 hours. When product is completely free of Lewis acid salt as evidenced by TLC, DCM from aqueous suspension was evaporated. The resulting precipitate containing product and inorganic salts werefiltered and washed with water. The dry crude product then stirred with 75 mL chloroform and filtered, residue washed with chloroform (75 mL). Combined filtrates evaporated to obtain pure product 8 (10.73 g, 93.1%), mp 136-137° C.; $R_f$=0.21 (petroleum ether:ethyl acetate, 2:1); ¹H NMR (400 MHz, CDCl₃) δ 1.05 (s, 3 H, 18-CH₃) 1.08 (s, 3 H, 19-CH₃) 3.19-3.32 (m, 1 H, 3α-H) 5.48 (d, J=5.38 Hz, 1 H, 6-H) 6.01 (dd, J=3.18, 1.71 Hz, 1 H,16-H) 7.29-7.37 (m, 2 H, Ar-5, 6-Hs) 7.47-7.56 (m, 1 H, Ar-7-H) 7.81-7.88 (m, 1H, Ar-4-H) 7.98 (s, 1 H, Ar-2-H); ¹³C NMR (101 MHZ, CDCl₃) δ 147.1, 143.2, 141.6, 140.2, 134.5, 124.0, 123.3, 122.4, 121.8, 120.2, 111.1, 61.0, 55.8, 50.4, 47.2, 38.1, 37.4, 36.8, 34.8, 31.0, 30.2, 27.8, 20.5, 19.2, 16.0; HPLC: $t_R$ 7.86 min 100%; HRMS calcd 414.2652 ($C_{26}H_{31}N_5H^+$), found 414.2653.

3α-Amino-17-(1H-benzimidazole-1-yl)androsta-5,16-diene (9): A solution of compound 6a (0.4 g, 0.97 mmol) and PPh₃ (1 sg, 3.97 mmol) in THF/MeOH/water (4/4/1 mL) was stirred at 60° C. for 10 hours. Solvents evaporated under vacuo, residue reconstituted with DCM (25 mL) and extracted with 1N HCl (20 mL×2). Combined aqueous extracts washed with DCM, then aqueous layer neutralized with 1N NaOH solution. Resulting solid filtered, washed with water and dried under vacuo to obtain pure 9 (0.25 g, 66.7%), mp 104-106° C.; $R_f$=0.2 (DCM:MeOH:TEA,10:1: 0.05); ¹H NMR (400 MHz, CDCl₃) δ 1.02 (s, 3 H, 18-CH₃), 1.07 (s, 3 H, 19-CH₃), 3.31 (br. s., 1 H, 3β-H), 5.47 (d, J=4.40 Hz, 1 H, 6-H), 5.93 (br. s., 1 H,16-H), 7.26-7.31 (m, 2 H, Ar-5, 6-Hs), 7.45-7.51 (m,1 H, Ar-7-H), 7.76-7.83 (m, 1 H, Ar-4-H), 7.95 (s, 1 H, Ar-2-H); ¹³C NMR (101 MHz, CDCl₃) δ 147.1, 143.2, 141.5, 138.4, 134.5, 123.8, 123.4, 123.3, 122.4, 120.1, 111.1, 55.7, 50.4, 47.2, 47.1, 38.8, 37.5, 34.8, 32.8, 31.1, 30.3, 30.2, 28.2, 18.8, 16.0; HPLC: $t_R$ 8.18 min 96.72%; HRMS calcd 388.2747 ($C_{26}H_{33}N_3H^+$), found 388.2747.

3β-Amino-17-(1H-benzimidazole-1-yl)androsta-5,16-diene (10): A solution of compound 8 (9 g, 21.77 mmol) and PPh₃ (22.85 a, 87.11 mmol) in THF/MeOH/water (145/145/36 mL) was stirred at 60° C. for 3 hours. Solvents evaporated under vacuo, residue reconstituted with DCM (200 mL). To this solution under stirring added 1N HCl (100 mL) and stirred for 5 minutes to obtain precipitate which collected by filtration (filtrate discarded). Solid product on Buchner funnel made slurry with DCM (20 mL), filtered and suck dried. The second filtrate collected and separately processed for second crop. The above solid product suspended in water (100 inL) and neutralized with aq. NaOH solution (1.25 g in 25 mL). The product filtered, washed with water (50 ml×3), suck dried and further dried under oven at 45-50° C. (7.36 g, 87.2%). For the second crop, second filtrate containing DCM and aqueous phase was treated with fresh 1N HCl (10 mL). The precipitate collected by filtration, solids treated with aq. NaOH solution, filtered and washed with water, and suck dried (0.275 g, 3.26%). Altogether 90.5% yield. mp 155-156° C.; $R_f$=0.2 (DCM:MeOH:TEA, 10:1:0.05); ¹H NMR (400 MHz, CDCl₃) δ 1.02 (s, 3 H, 18-C) 1.05 (s, 3 H, 19-CH₃) 2.58-2.69 (m, 1 H, 3α-H) 5.38 (d, J=4.89 Hz, 1 H, 6-H) 5.98 (dd, J=2.93, 1.71 Hz, 1 H,16-H) 7.47-7.52 (m, 1 H, 7-H) 7.78-7.85 (m, 1 H, Ar-4-H) 7.96 (s, 1 H, Ar-2-H); ¹³C NMR (101 MHz, CDCl₃) δ 147.2, 143.2, 142.1, 141.6, 134.5, 124.0, 123.3, 122.4, 120.1, 120.0, 111.1, 55.9, 51.9, 50.6, 47.2, 43.2, 38.0, 36.7, 34.9, 32.4, 31.0, 30.3, 30.3, 20.6, 19.3, 16.0; HPLC: $t_R$ 8.26 min 97.47%; HRMS calcd 388.2747 ($C_{26}H_{33}N_3H^+$), found 388.2747.

3α-(p-Nitrophenylcarbonyloxy)-17-(1H-benzimidazole-1-yl)-androsta-5,16-diene (11): To a two neck flask was added glaterone (1, 2 g, 5.15 mmol), 0.95 g (5.66 mmol) of pnitrobenzoicacid, 1.5 g (5.66 mmol) of PPh₃ and 30 mL anhydrous THF. The mixture was stirred until all solids dissolved and then cooled to 4° C. in an ice-water bath. A solution of 40% DEAD 2.46 mL (5.66 mmol) in anhydrous toluene was added drop wise, allowed to attain room temperature, stirred for 12 hours. The reaction mixture concentrated in vacuo and the resulting sticky residue was suspended in 5 mL of ethyl acetate, stirred, cooled and filtered. Mother liquor collected, stirred vigorously and 30 mL of petroleum ether added slowly. Resulting sticky suspension filtered, washed with 10% ethyl acetate in petroleum ether (25 mL) and dried under vacuo. The sticky solid made slurry on Buckner funnel with ether (7.5 mL×2), filtered and dried under vacuo. Free solids (0.8 g) obtained was a mixture of product 11, traces of tripheylphosphinoxide and diethyl 1,2-hydrazinedicarboxylate. The crude product dissolved in hot IPA, allowed to cool to room temperature, resulting precipitate filtered and dried under vacuo to obtain a white solid (0.5 g, 18.1%) of pure 11, mp 193-194° C.; $R_f$=0.4 (3% acetone in DCM); ¹H NMR (400 MHz, CDCl₃) δ 1.05 (s, 3 H, 18-CH₃), 1.13 (s, 3 H, 19-CH₃), 5.31 (br. s., 1 H, 3P-H), 5.39 (d, J=4.89 Hz, 1 H, 6-H), 6.00 (br. s., 1 H, 16-H), 7.28-7.34 (m, 2 H, Ar-5, 6-Hs), 7.48-7.52 (m, 1 H, Ar-7-H), 7.80-7.85 (m, 1 H, Ar-4-H), 7.97 (s, 1 H, Ar-2-H), 8.17 (m, J=8.80 Hz, 2 H, Ar'-2, 6-Hs), 8.30 (m, J=8.80 Hz, 2 H, Ar'-3, 5-Hs); ¹³C NMR (101 MHz, CDCl₃) δ 164.0, 150.4, 147.1, 141.6, 138.6, 136.4, 130.5, 124.1, 123.5, 123.4, 122.5, 122.0, 120.2, 111.1, 72.3, 55.8, 50.7, 47.2, 37.3, 36.4, 34.8, 33.9, 31.1, 30.3, 30.2, 26.2, 25.3, 20.4, 18.8, 16.0.

3α-Hydroxy-17-1H-benzimidazole-1-yl)androsta-5,16-diene (12): Ester 11 (0.5 g,0.93 mmol) was dissolved in THF/MeOH solvent mixture (2:1, 7.5 mL), and the resulting solution was treated with 1N aq. NaOH solution (1.25 mL). The mixture was stirred at ~22° C. for 2.5 hours and then solvents evaporated under vacuo at ~40° C. The residue solid treated with water, filtered, washed with water and dried to afford 12 (0.33 g, 91.2%) as a white solid, mp 203° C.; $R_f$=0.34 (DCM/MEOH/TEA, 10:0.5:0.025); ¹H NMR (400 MHz, CDCl₃) δ 1.02 (s, 3 H, 18-CH₃), 1.07 (s, 3 H, 19-CH₃), 4.05 (br. s., 1 H, 3β-H), 5.47 (d, J=4.89 Hz, 1 H, 6-H), 5.99 (br. s., 1 H, 16-H), 7.28-7.38 (m, Ar-5, 6-Hs), 7.50 (d, J=5.38 Hz, 1 H, Ar-7-H), 7.77-7.88 (m, 1 H, Ar-4-H), 7.97 (s, 1 H, Ar-2-H); ¹³C NMR (101 MHz, CDCl$_3$) δ 147.2, 143.2, 141.6, 139.1, 134.5, 124.1, 123.3, 123.1; 122.4, 120.2, 111.1, 67.0, 55.8, 50.6, 47.2, 39.8, 37.5, 34.8, 33.1, 31.1, 30.3, 30.2, 28.8, 20.3, 18.6, 16.0; HPLC: t$_R$ 1.89 min 99.28%; HRMS calcd 429.2587 (C$_{26}$H$_{32}$N$_2$OH$^+$). found 429.2587.

REFERENCES

1. Purushottamachar, P.; Godbole, A. M.; Gediya, L. K.; Martin, M. S.; Vasaitis, T. S.; Kwegyir-Afful, A. K.; Ramalingam, S.; Ates-Alagoz, Z.; Njar, V. C., Systematic structure modifications of multitarget prostate cancer drug candidate galeterone to produce novel androgen receptor down-regulating agents as an approach to treatment of advanced prostate cancer. *J Med Chem* 2013, 56, 4880-98.
2. Montgomery, B.; Eisenberger, M. A.; Rettig, M. B.; Chu, F.; Pili, R.; Stephenson, J. J.; Vogeizang, N. J.; Koletsky, A. J.; Nordquist, L. T.; Edenfield, W. J.; Mamlouk, K.; Ferrante, K. J.; Taplin, M. E., Androgen Receptor Modulation Optimized for Response (AR-MOR) Phase I and II Studies: Galeterone for the Treatment of Castration-Resistant Prostate Cancer. *Clin Cancer Res* 2016, 22, 1356-63.
3. Njar, V. C.; Brodie, A. M., Discovery and development of Galeterone (TOK-001 or VN/124-1) for the treatment of all stages of prostate cancer. *J Med Chem* 2015, 58, 2077-87.
4. Furic, L.; Rong, L.; Larsson, O.; Koumakpayi, I. H.; Yoshida, K.; Brueschke, A.; Petroulakis, E.; Robichaud, N.; Pollak, M.; Gaboury, L. A.; Pandolfi, P. P.; Saad, F.; Sonenberg, N., eIF4E phosphorylation promotes tumorigenesis and is associated with prostate cancer progression. *Proc Natl Acad Sci U S A* 2010, 107, 14134-9.
5. Graff, J. R.; Konicek, B. W.; Lynch, R. L.; Dumstorf, C. A.; Dowless, M. S.; McNulty, A. M.; Parsons, S. H.; Brail, L. H.; Colligan, B. M.; Koop, J. W.; Hurst, B. M.; Deddens, J. A.; Neubauer, B. L.; Stancato, L. F.; Carter, H. W.; Douglass, L. E.; Carter, J. H., eIF4E activation is commonly elevated in advanced human prostate cancers and significantly related to reduced patient survival. *Cancer Res* 2009, 69, 3866-73.
6. Lapointe, J.; Li, C.; Higgins, J. P.; van de Rijn, M.; Bair, E.; Montgomery, K.; Ferrari, M.; Egevad, L.; Rayford, W.; Bergerheim, U.; Ekman, P.; DeMarzo, A. M.; Tibshirani, R.; Botstein, D.; Brown, P. O.; Brooks, J. D.; Pollack, J. R., Gene expression profiling identifies clinically relevant subtypes of prostate cancer. *Proc Natl Acad Sci USA* 2004, 101, 811-6.
7. Tomlins, S. A.; Mehra, R.; Rhodes, D. R.; Cao, X.; Wang, L.; Dhanasekaran, S. M.; Kalyana-Sundaram, S.; Wei, J. T.; Rubin, M. A.; Pienta, K. J.; Shah, R. B.; Chinnaiyan, A. M., Integrative molecular concept modeling of prostate cancer progression. *Nat Genet* 2007, 39, 41-51.
8. Varambally, S.; Yu, J.; Laxman, B.; Rhodes, D. R.; Mehra, R.; Tomlins, S. A.; Shah, R. B.; Chandran, U.; Monzon, F. A.; Becich, M. J.; Wei, J. T.; Pienta, K. J.; Ghosh, D.; Rubin, M. A.; Chinnaiyan, A. M., Integrative genomic and proteomic analysis of prostate cancer reveals signatures of metastatic progression. *Cancer Cell* 2005, 8, 393-406.
9. Adesso, L.; Calabretta, S.; Barbagallo, F.; Capurso, G.; Pilozzi, E.; Geremia, R.; Delle Fave, G.; Sette, C., Gemcitabine triggers a pro-survival response in pancreatic cancer cells through activation of the MNK2/eIF4E pathway. *Oncogene* 2013, 32, 2848-57.
10. Martineau, Y.; Azar, R.; Muller, D.; Lasfargues, C.; El Khawand, S.; Anesia, R.;
Pelletier, J.; Bousquet, C.; Pyronnet, S., Pancreatic tumours escape from translational control through 4E-BP1 loss. *Oncogene* 2013, 33, 1367-1374.
11. Okitsu, K.; Kanda, T.; Imazeki, F.; Yonemitsu, Y.; Ray, R. B.; Chang, C.; Yokosuka, O., Involvement of interleukin-6 and androgen receptor signaling in pancreatic cancer. *Genes Cancer* 2010, 1, 859-67.
12. Robichaud, N.; Del Rincon, S. V.; Huor, B.; Alain, T.; Petruccelli, L. A.; Hearnden, J.; Goncalves, C.; Grotegut, S.; Spruck, C. H.; Furic, L.; Larsson, O.; Muller, W. J.; Miller, W. H.; Sonenberg, N., Phosphorylation of eIF4E promotes EMT and metastasis via translational control of SNAIL and MMP-3. *Oncogene* 2014.
13. Njar, V. C. O.; Purushottamachar, P. Nonsteroidal and steroidal compounds with potent androgen receptor down-regulation and anti prostate cancer activity. WO2014165815A2, 2014.
14. Purushottamachar, P.; Kwegyir-Afful, A. K.; Martin, M. S.; Ramamurthy, V. P.; Ramalingam, S.; Njar, V. C. O., Identification of Novel Steroidal Androgen Receptor Degrading Agents Inspired by Galeterone 3β-Imidazole Carbamate. *ACS Medicinal Chemistry Letters* 2016, 7, 708-713.
15. Aneja, R.; Davies, A. P.; Knaggs, J. A., Formation of a 3,5-cyclocholestan-6α-yl derivative in a nucleophillic substitution reaction of cholesterol. *Tetrahedron Letters* 1975, 16, 1033-1036.
16. Corey, E. J.; Nicolaou, K. C.; Shibasaki, M.; Machida, Y.; Shiner, C. S., Superoxide Ion as a Synthetically Useful Oxygen Nucleophile, *Tetrahedron Lett* 1975, /6, 3183-3186.
17. Freiberg, L. A., 6α-Azido-3α,5α-cyclocholestane. *J Org Chem* 1965, 30, 2476-2479.
18. Haworth, R. D.; Lunts, L. H. C.; McKenna, J., The constitution of conessine. VIII. Reaction of cholesteryl p-toiuenesulfonate with liquid ammonia. *J Chem. Soc.* 1955, 986-91.
19. Shoppee, C. W.; Summers, G. H. R., Steroids and Walden inversion. VII. The stereo chemistry and the mechanism of the iso-steroid rearrangement. *J. Chem. Soc.* 1952, 3361-74.
20. Winstein, S.; Adams, R., Role of neighboring groups in replacement reactions. XIV. The 5,6-double bond in cholesteryl p-toluenesulfonate as a neighboring group. *J. Am. Chem. Soc.* 1948, 70, 838-40.
21. Bruno, R. D.; Vasaitis, T. S.; Gediya, L. K.; Purushottamachar, P.; Godbole, A. M.; Ates-Alagoz, Z.; Brodie, A. M. H.; Njar, V. C. O., Synthesis and biological evaluations of putative metabolically stable analogs of VN/124-1 (TOK-001): Head to head anti-tumor efficacy evaluation of VN/124-1 (TOK-001) and abiraterone in LAPC-4 human prostate cancer xenograft model. *Steroids* 2011, 76, 1268-1279.
22. Debus, H., Ueber die Einwirkung des Ammoniaks auf Glyoxal. *Justus Liebigs Annalen der Chemie* 1858, 107, 199-208.
23. Chawla, A.; Sharma, A.; Sharma, A. k., Review: a convenient approach for the synthesis of imidazole derivatives using microwaves. *Pharma Chem.* 2012, 4, 116-140.

24. Sun, Q.; Cai, S.; Peterson, B. R., Practical synthesis of 3β-amino-5-cholestene and related 3β-halides involving i-steroid and retro-i-steroid rearrangements. *Org Lett* 2009, 11, 567-70.
25. Liu, F. W.; Liu, H. M.; Zhang, Y. B.; Zhang, J. Y.; Tian, L. H., Chlorination of 3beta-hydroxyl-S-Delta steroids with anhydrous ferric chloride. *Steroids* 2005, 70, 825-30.
26. Boonyarattanakalin, S.; Martin, S. E.; Dykstra, S. A.; Peterson, B. R., Synthetic mimics of small Mammalian cell surface receptors. *J Am Chem Soc* 2004, 126, 16379-86.
27. Pastor, I. M.; Torregrosa, R.; Yus, M., Isoprene-mediated lithiation of 1-alkylimidazoles: chiral induction of the alkyl substituent. *Lett. Org. Chem.* 2010, 7, 373-376.
28. Martinez, R.; Torregrosa, R.; Pastor, I. M.; Yus, M., Isoprene as lithiation mediator: synthesis of 2-substituted 1-alkylimidazole derivatives. *Synthesis* 2012, 44, 2630-2638.
29. Benoist, E.; Loussouam, A.; Remaud, P.; Chatal, J. F.; Gestin, J. F., Convenient and simplified approaches to N-monoprotected triaminopropane derivatives. Key intermediates for bifunctional chelating agent synthesis. *Synthesis* 1998, 1113-1118.
30. Chu, D.; Wang, B.; Ye, T. Preparation of steroidal CYP11B, CYP17, and/or CYP21 inhibitors for treating androgen-dependent conditions. WO2012083112A2, 2012.
31. Wu, P.; Wang, Q.; Gao, Q.; Wang, J.; Gu, H. Method for preparing sterol compound by inverting the hydroxy configuration. CN103396467A, 2013.
32. Myant, N. B., *The Biology of Cholesterol and Related Steroids*. Heinemann Medical Books1981; p 910.
33. Jilka, P., Millington C.; Elsegood, M. R. J.; Frese, J. W. A.; Teat, S.; Kimber, M. C., The selective mono and difunctionalization of carbocyclic cleft molecules with pyridyl groups and X-ray crystallographic analysis. *Tetrahedron* 2010, 66, 9327-9331.
34. Westaway, K. C.; Gao, Y.; Fang, Y. R., The effect of inert salts on the structure of the transition state in the $S_N2$ reaction between thiophenoxide ion and butyl chloride. *J Org Chem* 2003, 68, 3084-9.

The invention claimed is:

1. A process for preparing 3β-(1H-imidazole-1-yl)-17-(1H-benzimidazole-1-yl)-androsta-5,16-diene (2) and 3α-(1H-imidazole-1-yl)-17-(1H-benzimidazole-1-yl)-androsta-5,16-diene (5), the process comprising:

a first reaction comprising reacting a compound having Formula 1 (1)

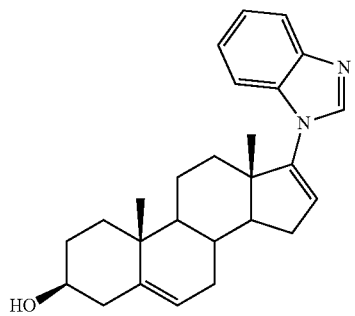

Formula 1 to produce 3-azido-17-(1H-benzimidazole-1-yl) androsta-5,16-diene (7, 8); and a second reaction comprising reacting the 3-azido-17-(1H-benzimidazole-1-yl) androsta-5,16-diene (7, 8) to produce 3-(1H-imidazole-1-yl)-17-(1H-benzimidazole-1-yl)-androsta-5,16-diene (2, 5), wherein:

the first reaction comprises mesylation of the compound having Formula 1 (1) to produce a mesylate (4), and azidation of the mesylate (4) comprising contacting the mesylate (4) with (i) an alkali metal azide to produce 3α-azido-17-(1H-benzimidazole-1-yl) androsta-5,16-diene (7) or (ii) an organic azide to produce 3β-azido-17-(1H-benzimidazole-1-yl) androsta-5,16-diene (8), wherein the 3α-azido-17-(1H-benzimidazole-1-yl) androsta-5,16-diene (7) is produced in a yield of at least 60% with a standard deviation of 2%, and the 3β-azido-17-(1H-benzimidazole-1-yl) androsta-5,16-diene (8) is produced in a yield of at least 93% with a standard deviation of 2%, and the second reaction comprises reduction of the 3α-azido-17-(1H-benzimidazole-1-yl) androsta-5,16-diene (7) and 3β-azido-17-(1H-benzimidazole-1-yl) androsta-5,16-diene (8) to produce an α-amine (9) and a β-amine (10), and cyclization of the α-amine (9) and β-amine (10) to produce the 3β-(1H-imidazole-1-yl)-17-(1H-benzimidazole-1-yl)-androsta-5,16-diene (2) and 3α-(1H-imidazole-1-yl)-17-(1H-benzimidazole-1-yl)-androsta-5,16-diene (5).

2. The process according to claim 1, wherein the azidation comprises contacting the mesylate (4) with (i) the alkali metal azide or (ii) the organic azide, so as to perform the azidation in a stereo-selective manner to produce (i) the 3α-azido-17-(1H-benzimidazole-1-yl) androsta-5,16-diene (7) and (ii) the 3β-azido-17-(1H-benzimidazole-1-yl) androsta-5,16-diene (8).

3. The process according to claim 2, wherein the azidation further comprises contacting the mesylate (4) with trimethylsilyl azide in the presence of boron trifluoride etherate and dichloromethane to produce the 3β-azido-17-(1H-benzimidazole-1-yl) androsta-5,16-diene (8).

4. The process according to claim 3, wherein 15 equivalents of the trimethylsilyl azide and 27 equivalents of the boron trifluoride etherate are added for 1 equivalent of the mesylate (4).

5. The process according to claim 1, wherein the reduction and the cyclization are performed in a stereo-retentive manner.

6. The process according to claim 1, wherein the process produces a yield of the 3β-(1H-imidazole-1-yl)-17-(1H-benzimidazole-1-yl)-androsta-5,16-diene (2) of at least 62.8% with a standard deviation of 2%.

7. The process according to claim 1, wherein the process produces a yield of the 3α-(1H-imidazole-1-yl)-17-(1H-benzimidazole-1-yl)-androsta-5,16-diene (5) of at least 28% with a standard deviation of 2%.

* * * * *